United States Patent [19]

Chiarelli et al.

[11] Patent Number: 6,069,246

[45] Date of Patent: May 30, 2000

[54] METHOD FOR TREATING LACTAMS

[75] Inventors: Henri Chiarelli, Communay; Philippe Leconte, Meyzieu, both of France

[73] Assignee: Rhodia Fiber & Resin Intermediates, Courbevoie Cedex, France

[21] Appl. No.: 09/297,016

[22] PCT Filed: Oct. 23, 1997

[86] PCT No.: PCT/FR97/01903

§ 371 Date: Jul. 27, 1999

§ 102(e) Date: Jul. 27, 1999

[87] PCT Pub. No.: WO98/17641

PCT Pub. Date: Apr. 30, 1998

[30] Foreign Application Priority Data

Oct. 24, 1996 [FR] France .................................. 96 13203

[51] Int. Cl.$^7$ ................................................. C07D 201/08
[52] U.S. Cl. ............................................................. 540/540
[58] Field of Search ............................................... 540/540

[56] References Cited

FOREIGN PATENT DOCUMENTS 0 659 741 of 0000 European Pat. Off. .
96 22974 of 0000 WIPO .

*Primary Examiner*—Mukund J. Shah
*Assistant Examiner*—Bruck Kifle
*Attorney, Agent, or Firm*—Burns, Doane, Swecker & Mathis, L.L.P.

[57] ABSTRACT

The present invention relates to the treatment of lactams obtained directly from their synthesis process, avoiding the formation of oligomers as far as possible. The invention consists, more precisely, of a process for treating a lactam using the reaction flow obtained from a cyclizing hydrolysis of an aminonitrile, characterized in that the reaction flow leaving the hydrolysis reactor is cooled, over a period of less than or equal to 1 hour, to a temperature below or equal to 150° C. before it is fractionated.

12 Claims, No Drawings

METHOD FOR TREATING LACTAMS

The present invention relates to the treatment of lactams obtained directly from their synthesis process, avoiding the formation of oligomers as far as possible.

Lactams, and more particularly caprolactam which is the starting material for polyamide 6, are generally distilled in order to be separated from the compounds from which they have been prepared and from the by-products also formed during their synthesis.

Caprolactam is prepared industrially in a conventional manner by a Beckmann rearrangement reaction of cyclohexanone oxime with sulphuric acid or oleum, followed by neutralization of the medium with ammonia and then separation and purification of the caprolactam.

Lactams may also be obtained by cyclizing hydrolysis of aminonitriles. They must then be separated from the ammonia formed, the unreacted water, any solvent used, light organic compounds (that is to say those having a boiling point below that of the lactam), any unconverted aminonitrile, as well as heavier organic compounds (with a boiling point higher than that of the lactam).

Purification of the lactam, mainly by distillation, and more particularly its separation from water, is not always carried out immediately on leaving the cyclizing hydrolysis reactor.

It has been observed that lactam oligomers are formed when the reaction flow leaving the hydrolysis reactor is maintained at a temperature above about 50° C. for a relatively long period of time. This is because maintaining the reaction mixture in the liquid condensed phase leads to the formation of oligomers.

Similarly, it has been observed that if the average residence time of the lactam in the distillation apparatus exceeds about one hour at a temperature above 100° C., oligomers are also formed.

In addition, when the lactam is not distilled immediately after it has been prepared, the said lactam is sometimes stored for a period which may be relatively long, that is to say, as a guide, equal to several hours.

It has been observed that storage of the crude lactam for a period of a few hours, especially in solution, at a temperature equal to or above 50° C. leads to the formation of oligomers of the said lactam.

Depending on the apparatus used, the presence of these oligomers formed during the various phases of the treatment of the flow obtained from the cyclizing hydrolysis reaction is liable to cause blockages, especially in the pipes between the reactor and the distillation column or the storage tank. In addition, the formation of oligomers reduces the overall yield of lactam and creates additional problems of purification and recycling.

The present invention overcomes these drawbacks by limiting the formation of lactam oligomers as far as possible.

The invention consists, more precisely, of a process for treating a lactam using the reaction flow obtained from a vapour-phase cyclizing hydrolysis of an aminonitrile, characterized in that the reaction flow leaving the hydrolysis reactor is cooled, over a period of less than or equal to 1 hour, to a temperature below or equal to 150° C. before it is fractionated.

The cooling may be carried out in industrial processes by a heat exchanger with circulation of water, of air or, where appropriate, of vapour or heat-exchange fluid.

In practice, an implementation variant of the cooling will consist in recovering the calories from the reaction mixture obtained from the hydrolysis reaction.

These calories may be used directly to preheat a heat-exchange fluid which may then serve to preheat the reactants of the cyclizing hydrolysis, that is to say, essentially, the aminonitrile and the water.

They may also serve to preheat the steam used to heat the hydrolysis reactor.

They may also serve to generate steam which will be used in one or other phase of the process for the preparation of lactams.

This recovery of the calories from the mixture obtained from the cyclizing hydrolysis reaction may be supplemented by cooling with water or air, when the temperature of the said mixture reaches a value below 150° C. or preferably below 100° C.

In the present text, the term cooling covers the various modes of production indicated above, or equivalent modes.

When the reaction flow is distilled immediately, that is to say without storage, it is preferable, for the economy of the process, to cool the said flow over the shortest possible period, preferably less than or equal to 10 minutes, to a temperature of from 50° C. to 150° C. and preferably from 70° C. to 120° C. It is also recommended to limit the duration of feeding of the distillation column, that is to say the time which elapses between the reaction flow leaving the hydrolysis reactor and the actual distillation, to a maximum of one hour and preferably to 30 minutes. The distillation itself is carried out such that the average residence time of the lactam in the distillation apparatus is less than or equal to 1 hour.

When the reaction flow is not treated immediately and is stored for a period of longer than 1 hour, the cooling is carried out over a period of less than or equal to 10 minutes and preferably to a temperature below or equal to 50° C.

The lactam used in the present process is more particularly chosen from those which are obtained by vapour-phase cyclizing hydrolysis of an aliphatic aminonitrile of general formula (I):

in which R represents a linear or branched alkylene radical having from 3 to 12 carbon atoms.

Among the lactams, mention may be made more particularly of those which serve as starting material for the preparation of polyamides 4, 5, 6 and 11 and which are obtained from the aminonitriles of formula (I), in which the symbol R represents a linear alkylene radical having 3, 4, 5 or 10 carbon atoms.

As indicated above, the caprolactam whose polymerization gives polyamide 6, which is prepared from 6-aminocapronitrile (or epsilon-capronitrile), is the lactam preferentially used in the process of the invention.

By way of a non-limiting illustration of the process for the preparation of lactams, by vapour-phase cyclizing hydrolysis of aminonitriles of formula (I), reference may be made, for example, to Patents EP-A-0,659,741 or WO-A-96/22974.

The lactam to be purified is generally in the form of an aqueous or alcoholic solution. Since the cyclizing hydrolysis is carried out in the vapour phase, the said lactam obtained is, more often than not, in aqueous solution. The lactam concentration of such a solution is generally from 20% to 80% on a weight for weight basis. The aminonitrile usually represents up to 15% of the weight of the lactam, and most frequently from 0% to 10% of this weight.

The process of the invention generally makes it possible to limit the formation of oligomers to a content such that the phenomenon has virtually no adverse effect. Such a content is generally less than or equal to 2% by weight of oligomers per unit weight of lactam and preferably less than or equal to 1% on a weight for weight basis.

Preferably, in the process of the invention, the lactam is stored at a temperature below or equal to 40° C. before being distilled if the storage period is longer than or equal to 1 hour, and/or the distillation is carried out such that the average residence time of the lactam in the distillation apparatus is less than or equal to 30 minutes.

The examples which follow illustrate the invention.

EXAMPLE 1

The cyclizing hydrolysis of 6-aminocapronitrile is carried out by passing 91 g/h of this compound and 85 g/h of water over 53 ml (22.7 g) of alumina at 300° C.

At the reactor outlet, the gases are cooled rapidly (less than 5 minutes) to room temperature (about 20° C.).

A clear aqueous ammoniacal solution is obtained containing (chromatographic assay) 47.5% by weight of caprolactam and 2.9% by weight of aminocapronitrile. This corresponds to a degree of conversion (DC) of the aminocapronitrile of 94% and to a yield of caprolactam relative to the aminocapronitrile loaded (RY) of 93% (i.e. a selectivity towards caprolactam relative to the aminocapronitrile converted, or CY, of 99%).

This solution is stored for 3 months at a temperature of about 20° C. and is then reassayed by chromatography. No presence of precipitate is observed. 48% by weight of caprolactam and 2.7% by weight of aminocapronitrile are then found, which, bearing in mind the precision of the assays, means that these crude solutions of caprolactam are stable under these conditions.

Comparative Test 1

An aqueous solution containing 50% by weight of an equimolar mixture of caprolactam and ammonia is maintained at 150° C. for 6 hours. By assaying, it is observed that 10% of the caprolactam has been converted, while a red-brown precipitate has been formed.

EXAMPLE 2

The cyclizing hydrolysis of 6-aminocapronitrile is carried out by passing 100 g/h of this compound and 64 g/h of water over 200 ml (135 g) of alumina at 300° C.

At the reactor outlet, the gases are cooled rapidly (less than 5 minutes) to room temperature (about 20° C.).

A clear aqueous ammoniacal solution is obtained containing (chromatographic assay) caprolactam and aminocapronitrile in amounts corresponding to a degree of conversion of the aminocapronitrile of 95.5% and to a yield of caprolactam relative to the aminocapronitrile loaded of 95.5% (i.e. a selectivity towards caprolactam relative to the aminocapronitrile converted of 100%).

Comparative Test 2

The cyclizing hydrolysis of 6-aminocapronitrile is carried out by passing 100 g/h of this compound and 64 g/h of water over 200 ml (135 g) of the alumina used in Example 2 at 300° C.

At the reactor outlet, the reaction flow is cooled and maintained at about 150° C. for two hours (in total), before being cooled over 10 seconds to room temperature (about 20° C.). During this period of maintenance at 150° C., the flow then includes a gaseous phase and a liquid condensed phase.

An aqueous ammoniacal solution is obtained containing (chromatographic assay) caprolactam and aminocapronitrile in amounts corresponding to a degree of conversion of the aminocapronitrile of 98.5% and a yield of caprolactam relative to the aminocapronitrile loaded of 94% (i.e. a selectivity towards caprolactam relative to the aminocapronitrile converted of only 95%). This solution contains a precipitate of caprolactam oligomers.

What is claimed is:

1. Process for separating a lactam from the reaction flow obtained from a vapour-phase cyclizing hydrolysis of an aminonitrile, wherein the reaction flow leaving the hydrolysis reactor is cooled, over a period of less than or equal to 1 hour:

to a temperature below or equal to 150° C. before it is distilled.

or, to a temperature of less than or equal to 50° C. before being stored for a period of longer than 1 hour, before it is fractionated.

2. Process according to claim 1, wherein the reaction flow is cooled to a temperature of from 70° C. to 120° C. before being distilled.

3. Process according to claim 2, wherein the reaction flow is cooled over a period of less than or equal to 10 minutes.

4. Process according to claim 2, wherein the duration of feeding of the distillation column, or the time which elapses between the reaction flow leaving the hydrolysis reactor and the actual distillation, is limited to a maximum of one hour.

5. Process according to claim 2 wherein the distillation is carried out such that the average residence time of the lactam in the distillation apparatus is less than or equal to 1 hour.

6. Process according to claim 1, wherein the cooling of the reaction flow is carried out over a period of less than or equal to 10 minutes and to a temperature below or equal to 50° C. before being stored for a period of longer than 1 hour.

7. Process according to one of claim 1 wherein the lactam comprises those obtained by vapour-phase cyclizing hydrolysis of an aliphatic aminonitrile of formula (I):

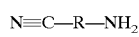

in which R represents a linear or branched alkylene radical having from 3 to 12 carbon atoms.

8. Process according to one of claim 1 wherein the lactam used comprises those obtained by vapour-phase cyclizing hydrolysis of an aliphatic aminonitrile of formula (I), in which R represents a linear alkylene radical having 3, 4, 5 or 10 carbon atoms.

9. Process according to one of claim 1 wherein the lactam used is caprolactam.

10. Process according to claim 5, wherein the distillation is carried out such that the average residence time of the lactam in the distillation apparatus is less than or equal to 30 minutes.

11. Process according to claim 6, wherein the lactam is stored at a temperature below or equal to 40° C. before being stored for a period of longer than or equal to 1 hour.

12. Process according to claim 4, wherein the time is limited to a maximum of thirty minutes.

* * * * *